United States Patent

Kudo et al.

[11] Patent Number: 6,162,621
[45] Date of Patent: Dec. 19, 2000

[54] PROCESS FOR PRODUCING OPTICALLY ACTIVE AZETIDINE-2-CARBOXYLIC ACID DERIVATIVE

[75] Inventors: Junko Kudo, Ibaraki; Motoo Hazama, Toyonaka; Norihiko Hirata, Suita, all of Japan

[73] Assignee: Sumitomo Chemical Company, Ltd., Osaka, Japan

[21] Appl. No.: 09/012,227

[22] Filed: Jan. 23, 1998

[30] Foreign Application Priority Data

| Jan. 24, 1997 | [JP] | Japan | 9-011326 |
| Jun. 3, 1997 | [JP] | Japan | 9-145443 |
| Jul. 11, 1997 | [JP] | Japan | 9-186363 |

[51] Int. Cl.⁷ .................................................. C12P 17/10
[52] U.S. Cl. ............................................................ 435/121
[58] Field of Search ............................................. 435/121

[56] References Cited

FOREIGN PATENT DOCUMENTS

| 0197474A2 | 10/1986 | European Pat. Off. . |
| 0552041A2 | 7/1993 | European Pat. Off. . |
| 0634492A1 | 1/1995 | European Pat. Off. . |
| 49-014457 | 2/1974 | Japan . |
| 9702241 | 1/1997 | WIPO . |
| WO97/02241A1 | 1/1997 | WIPO . |
| 9802568 | 1/1998 | WIPO . |

OTHER PUBLICATIONS

Rodebaugh et al., J. Heterocyclic Chemistry, vol. 6, No. 6, pp. 993–994 (Dec. 1969).

Kozikowski et al., J. Med. Chem., 1993, 36, 2706–2708.

D. Seebach et al., Liebigs Ann. Chem., 687–695 (1990).

*Primary Examiner*—Herbert J. Lilling
*Attorney, Agent, or Firm*—Birch, Stewart, Kolasch & Birch, LLP.

[57] ABSTRACT

There is provided a process for producing N-substituted azetidine-.2-carboxylic acid of the formula I:

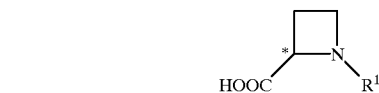

wherein $R^1$ denotes an aralkyl group or an arylated lower alkoxycarbonyl group and * designates an asymmetric carbon atom, which is characterized by:

reacting an N-substituted azetidine-2-carboxylic acid ester of the formula II:

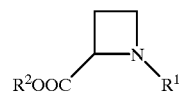

wherein $R^1$ has the same meaning as defined above and $R^2$ denotes an alkyl group, an aralkyl group or an allyl group, with an enzyme capable of selectively hydrolyzing a stereoisomer based on the carbon atom of the 2-position of the azetidine ring.

9 Claims, No Drawings

PROCESS FOR PRODUCING OPTICALLY ACTIVE AZETIDINE-2-CARBOXYLIC ACID DERIVATIVE

FIELD OF THE INVENTION

The present invention relates to a process for producing an optically active azetidine-2-carboxylic acid derivative.

DESCRIPTION OF THE RELATED ART

Optically active azetidine-2-carboxylic acid has been known as an intermediate for producing a pharmaceutical such as the antithrombotic agent disclosed in EP 542525.

Optically active azetidine-2-carboxylic acid has been produced by a process which has the following steps:
reacting azetidine-2-carboxylic acid, which is obtained by a process disclosed in Journal of Heterocyclic Chemistry, 6, 435 (1969), with benzyloxycarbonyl chloride to give N-(benzyloxycarbonyl)azetidine-2-carboxylic acid,
subjecting N-(benzyloxycarbonyl)-azetidine-2-carboxylic acid to optical resolution using an optically active tyrosine hydrazine, and then
subjecting the obtained optically active N-(benzyloxycarbonyl)-azetidine-2-carboxylic acid to hydrogenolysis to give an optically active azetidine-2-carboxylic acid [Journal of Heterocyclic Chemistry, 6, 993 (1969)].

The prior art methods for preparing optically active azetidine-2-carboxylic acid, however, had difficulties in that they require, as a reagent for optical resolution, an optically active tyrosine hydrazine which is expensive and not readily available on an industrial scale.

SUMMARY OF THE INVENTION

Therefore, an object of the invention is to provide a process for producing the desired compound in a simple step.

The present invention provides:

1. a process for producing N-substituted azetidine-2-carboxylic acid of the formula I:

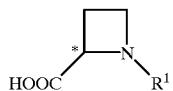

wherein $R^1$ denotes an aralkyl group or an arylated lower alkoxycarbonyl group and * designates an asymmetric carbon atom, which comprises:
reacting an N-substituted azetidine-2-carboxylic acid ester of the formula II:

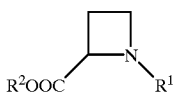

wherein $R^1$ has the same meaning as defined above and $R^2$ denotes an alkyl group, an aralkyl group or an allyl group, with an enzyme capable of selectively hydrolyzing a stereoisomer based on the carbon atom of the 2-position of the azetidine ring;

2. a process for producing an optically active azetidine-2-carboxylic acid of the formula III:

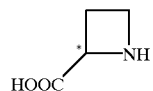

wherein * designates an asymmetric carbon atom, which comprises: reacting the optically active N-substituted azetidine-2-carboxylic acid of the formula I as defined above obtainable according to the method described in item 1 above, with a reducing agent in the presence of a catalyst; and 3. a process for improving optical purity of azetidine-2-carboxylic acid of the formula III as defined above, which comprises:
preparing a solution of azetidine-2-carboxylic acid; and
cooling the said solution in the presence of a seed crystal of one optional optical isomer of the azetidine-2-carboxylic acid to selectively recrystalize the optical isomer of the azetidine-2-carboxylic acid having the same configuration with respect to the carbon atom of the 2-position of the azetidine ring as the seed crystal.

DESCRIPTION OF THE PREFERRED EMBODIMENT

First description will be made to the process for producing N-substituted azetidine-2-carboxylic acid of the formula I as defined above, which comprises:
reacting an N-substituted azetidine-2-carboxylic acid ester of the formula II as defined above with an enzyme capable of selectively hydrolyzing a stereoisomer based on the carbon atom of the 2-position of the azetidine ring.

The aralkyl group for $R^1$ in the N-substituted azetidine-2-carboxylic acid ester of the formula I includes a benzyl group, a phenethyl group and a phenylpropyl group, all of which may have an asymmetric carbon and further include a benzhydryl group and a triphenylmethyl group.

The arylated lower alkoxycarbonyl group for $R^1$ includes a $(C_1-C_2)$alkoxyl group having a phenyl substituent which may be substituted with, for example, a benzyloxycarbonyl group, a p-nitrobenzyloxycarbonyl group and a 2-phenylethyloxycarbonyl group.

Examples of the alkyl group for $R^2$ include a $(C_1-C_8)$ alkyl group such as a methyl group, an ethyl group, a propyl group such as n-propyl or i-propyl, and a butyl group such as n-butyl, sec-butyl, i-butyl or t-butyl group.

Examples of the aralkyl group for $R^2$ include a benzyl group, a phenethyl group and a phenylpropyl group, all of which may have an asymmetric carbon.

An example of the aryl group for $R^2$ includes a phenyl group.

Specific examples of the N-substituted azetidine-2-carboxylic acid ester include: for example,
methyl N-benzylazetidine-2-carboxylate,
methyl N-[(S)-phenylethyl]azetidine-2-carboxylate,
methyl N-[(R)-phenylethyl]azetidine-2-carboxylate,
methyl N-phenylpropylazetidine-2-carboxylate,
methyl N-benzhydrylazetidine-2-carboxylate,
methyl N-triphenylmethylazetidine-2-carboxylate,
and corresponding an ethyl, a propyl group such as n-propyl, or i-propyl ester, or a butyl such as n-butyl, sec-butyl, i-butyl, or t-butyl ester.

The N-substituted azetidine-2-carboxylic acid ester of the formula II has two stereoisomer based on the carbon atom of the 2-position of the azetidine ring, therefore it may be a racemic mixture of both of the stereoisomers or may contain an excess amount of one stereoisomer.

The enzyme of the present invention which is capable of selectively hydrolyzing a stereoisomer based on the carbon atom of the 2-position of the azetidine ring may be anyone derived from a microorganism, an animal, a plant.

Examples of the enzyme derived from a microorganism include such an enzyme belonging to Candida, Mucor, Humicola, Rhizopus, Aspergillus, Penicillium, Bacillus, Arthrobacter, Pseudomonas, Chromobacterium, Alkaligenes or Achromobacter. An enzyme produced by a transformant microorganism transformed by introducing the gene coding for the enzyme of interest also can be used. The said microorganisms can be readily cultured by such a conventional method as liquid culturing which comprises inoculating the said microorganisms to a sterilized liquid culture and culturing at 20 to 40° C. under shaking, or by solid culturing, if necessary.

The enzymes may be purchased commercially. Examples of the commercially available enzyme include: Chirazyme L-2 (originated from *Candida antarctica,* Product of Boehringer Mannheim Com., Ltd), Novozyme 435 (originated from *Candida antarctica,* Product of Novo-Nordisk Com., Ltd), Lipase AY (originated from *Candida rugosa,* Product of Amano Phrmaceuticals Com., Lts) and Lipase MY (originated from *Candida cylindracea,* Meito Sangyo Com., Ltd).

Examples of the animal derived enzyme include, for example, Steapsin or Pancreatin of sheep or hog internals.

An example of the plant derived enzyme includes an enzyme of wheat germ.

These enzymes can be used in various forms, for example, in a form of purified enzyme, crude enzyme, culture broth of microorganism, culture, cell-culture or treated product thereof. The enzyme or cells can be used in a form of immobilized enzyme or immobilized cells.

The amount of the enzyme to be used is optionally set in a range within which deferring of the reaction product should not occur of the selectivity of the reaction should not lower.

For example, the amount of the commercially available enzyme is 0.001 to 0.5 parts by weight, preferably 0.002 to 0.2 parts by weight based on one part by weight of the N-substituted azetidine-2-carboxylic acid ester.

The reaction of the enzyme and the N-substituted azetidine-2-carboxylic acid ester is usually conducted in an aqueous solution, which may be an aqueous buffer solution. Examples of the buffer solution include those of inorganic acid salts such as an aqueous solution of alkali metal phosphate salt (e.g., aqueous sodium phosphate, aqueous potassium phosphate) or aqueous buffer solution of an organic acid salt such alkali metal acetate (e.g., aqueous solution of sodium acetate, potassium acetate).

The amount of the aqueous solution to be used is usually not less than 0.5 mole per mol of the N-substituted azetidine-2-carboxylic acid ester, or not more than 100 parts by weight per 1 part by weight of the ester.

The reaction can also be conducted in the presence of a hydrophobic organic solvent or a hydrophilic organic solvent. These solvents are preferably used to improve the optical purity of the obtained N-substituted azetidine-2-carboxylic acid ester.

Examples of the hydrophobic organic solvent include an ether solvent such as t-butyl methyl ester or isopropyl ether, and a hydrocarbon solvent such as toluene, hexane, cyclohexane or heptane.

Examples of the hydrophilic organic solvent include an alcohol such as t-butanol, methanol, ethanol, isopropanol or n-butanol, an ether such as tetrahydrofuran, a sulfoxide such as dimethyl sulfoxide, ketone such as acetone, and a nitrile such as acetonitrile. These hydrophobic organic solvents or hydrophilic organic solvents are used alone or as a mixture containing two or more thereof respectively, or each other.

When an organic solvent is used, the amount of the solvent to be used is usually not more than 100 parts by weight, preferably within a range of 0.1 to 50 parts by weight per 1 part by weight of the N-substituted azetidine-2-carboxylic acid ester.

The reaction is usually carried out by mixing water, N-substituted azetidine-2-carboxylic acid ester and the enzyme of the present invention. When the organic solvent is used, the ester, enzyme and water can be mixed in the organic solvent.

The hydrolysis reaction can be conducted at an optionally set pH range and is usually conducted at pH 4 to 10.

The reaction temperature is usually set within a region where the stability of the enzyme and the reaction velocity are not adversely affected, the reaction temperature is, for example, 5 to 65° C., preferably 20 to 50° C.

In the present hydrolysis reaction, a stereoisomer having an asymmetric carbon atom designated by * is subjected to hydrolysis reaction preferentially with retention of the configuration at the carbon atom to produce a desired optically active N-substituted azetidine-2-carboxylic acid.

After completion of the hydrolysis reaction, the reaction is subjected to a conventional post-treatment method such as phase separation in which appropriate amount of water or hydrophobic organic solvent may be added and/or extraction with an hydrophobic organic solvent, if necessary.

Examples of the hydrophobic organic solvent include an ether such as t-butyl methyl ether or isopropyl ether, a hydrocarbon solvent such as toluene, hexane, cyclohexane or heptane, a halogenated hydrocarbon solvent such as dichloromethane, dichloroethane, chloroform, chlorobenzene or o-dichlorobenzene, and an ester such as ethyl acetate, methyl acetate or butyl acetate.

After phase separation or extraction, the obtained aqueous phase is usually subjected to evaporation to remove water to obtain the desired optically active N-substituted azetidine-2-carboxylic acid, which may be further purified by recrystalization or column chromatography, if necessary.

Specific examples of the optically active N-substituted azetidine-2-carboxylic acid include:

N-substituted azetidine-2-carboxylic acid having (S)-configuration such as
(S)-N-benzylazetidine-2-carboxylic acid,
(S)-N[(S)-phenylethyl]azetidine-2-carboxylic acid,
(S)-N-[(R)-phenylethyl]azetidine-2-carboxylic acid, and
(S)-N-(phenylpropyl)azetidine-2-carboxylic acid,
(S)-N-benzhydrylazetidine-2-carboxylic acid,
(S)-N-triphenylmethylazetidine-2-carboxylic acid; and
N-substituted azetidine-2-carboxylic acid having (R)-configuration such as
(R)-N-benzylazetidine-2-carboxylic acid,
(R)-N-[(S)-phenylethyl]azetidine-2-carboxylic acid,
(R)-N-[(R)-phenylethyl]azetidine-2-carboxylic acid,
(R)-N-(phenylpropyl)azetidine-2-carboxylic acid,
(R)-N-benzhydrylazetidine-2-carboxylic acid, and
(R)-N-triphenylmethylazetidine-2-carboxylic acid.

The other stereoisomer of the N-substituted azetidine-2-carboxylic acid ester which had not been hydrolyzed can be recovered by extraction with a hydrophobic organic solvent.

Next, description will be made to the process for producing an optically active azetidine-2-carboxylic acid of the formula III as defined above, which comprises:
reacting the optically active N-substituted azetidine-2-carboxylic acid of the formula I obtainable according to the method as defined above with a reducing agent in the presence of a catalyst.

The catalyst to be used in this reaction includes, for example, noble metal catalyst such as palladium carbon, palladium hydroxide carbon, palladium acetate, palladium chloride, palladium oxide and palladium hydroxide. The amount of the catalyst is usually 0.0001 to 0.5 part by weight per 1 part by weight of the optically active N-substituted azetidine-2-carboxylic acid.

Examples of the reducing agent include hydrogen, hydrazine or a salt thereof such as hydrazine hydrochloride, sulfate or acetate salt, or formic acid or a salt thereof such as ammonium formate.

The reaction is usually conducted in a solvent. Examples of the solvent include: water, an alcohol solvent such as methanol, ethanol or 2-propanol, an ester solvent such as ethyl acetate, methyl acetate or butyl acetate, a nitrile solvent such as acetonitrile, an aromatic hydrocarbon solvent such as toluene, xylene or benzene, an aliphatic hydrocarbon solvent such as hexane or heptane, a halogenated hydrocarbon solvent such as dichloromethane, dichloroethane, chloroform, chlorobenzene or o-dichlorobenzene, an ether solvent such as diethyl ester or t-butyl methyl ether, an amide solvent such as acetamide, N,N-dimethylformamide or N,N-dimethylacetamide. These solvents can be used alone or in combination thereof. The amount of the solvent to be used is usually 2 to 100 parts by weight per 1 part by weight of the optically active N-substituted azetidine-2-carboxylic acid.

When hydrogen is employed as a reducing agent, hydrogen is supplied into a solution of N-substituted azetidine-2-carboxylic acid and catalyst. The hydrogen gas may be supplied into the reaction solution or the reaction can be conducted in a hydrogen atmosphere at normal pressure to compressed pressure under stirring.

When a reducing agent other than hydrogen is employed, the reducing agent can be added to a solution of N-substituted azetidine-2-carboxylic acid and catalyst.

The reaction temperature is usually within a range of −50 to 200° C.

After completion of the reaction, the optically active azetidine-2-carboxylic acid can be readily obtained or isolated by a conventional treatment such as filtration of the catalyst, and evaporation of the solvent. The obtained product may be further purified by recrystalization or column chromatography, if necessary.

The reduction process yields the desired product of the formula III with retention of the configuration.

Finally, a description will be made to the third process of the present invention, that is, a process for improving optical purity of azetidine-2-carboxylic acid of the formula III as defined above, which comprises:

preparing a solution of azetidine-2-carboxylic acid; and
cooling the said solution in the presence of a seed crystal of one optional optical isomer of the azetidine-2-carboxylic acid to selectively recrystalize the optical isomer of the azetidine-2-carboxylic acid having the same configuration with respect to the carbon atom of the 2-position of the azetidine ring as the seed crystal.

Azetidine-2-carboxylic acid of the formula III that can be purified by the present process consists of two enantiomers, which are preferred to as D-isomer and L-isomer respectively, the ratio of the two enatiomers being not limited, however, enantio excess isomer of azetidine-2-carboxylic acid is preferably used. For example, azetidine-2-carboxylic acid having optical purity of not less than 60%ee is preferred.

The solvent to be used for preparing the solution of azetidine-2-carboxylic acid is not particularly limited, and any solvent that can dissolve azetidine-2-carboxylic acid to form a uniform solution can be employed.

Water or a water miscible hydrophilic organic solvent or a mixture thereof are preferably used.

Examples of the hydrophilic organic solvent include: an alcohol solvent such as methanol, ethanol, 1-propanol, 2-propanol or ethyleneglycol, a carboxylic acid solvent such as formic acid or acetic acid, an ether solvent such as tetrahydrofurane, dioxane, monoglyme(ethyleneglycol dimethyl ether) or diglyme(diethyleneglycol dimethyl ether), or acetone, acetonitrile, N,N-dimethylformamide, N,N-dimethylacetamide, or dimethylsulfoxide. These solvent may be used alone or in combination thereof. Preferred solvents are methanol or ethanol among the hydrophilic organic solvents and a mixed solvent of water and methanol or ethanol the ratio of which is not particularly limited.

Azetidine-2-carboxylic acid is usually dissolved in a solvent at 0° C. to the boiling point of the solvent used, preferably, at not less than room temperature, more preferably not less than 30° C., further preferably, not less than 50° C. in terms of the yield.

The amount of the solvent to be used varies with the kind of the solvent. At least such an amount of the solvent that can dissolve the azetidine-2-carboxylic acid at a temperature not more than the boiling temperature of the used solvent, and as minimum as possible amount of the solvent are preferred in terms of the yield. In other words, the amount is preferably 1 to 1.1 times amount of the solvent that makes a saturated solution of azetidine-2-carboxylic acid at a certain dissolving temperature. Such amount of the solvent can be determined by a conventional method beforehand.

Cooling of the thus prepared solution of azetidine-2-carboxylic acid is conducted at a rate of 1 to 50° C. per hour, preferably 3 to 20° C. The cooling rate does not have to be constant but can be varied consecutively or in a stepwise manner.

The final temperature of the solution reached by cooling can be optional set and is usually in a range of −80 to +50° C., preferably −50 to +30° C., more preferably −30 to +10°.

Cooling of the said solution in the presence of a seed crystal of one optional optical isomer of the azetidine-2-carboxylic acid to selectively recrystalize the optical isomer of the azetidine-2-carboxylic acid having the same configuration with respect to the carbon atom of the 2-position of the azetidine ring as the seed crystal.

Usually a seed crystal having the same configuration with respect to the carbon atom at 2-position as the excess isomer present in the mixture of azetidine-2-carboxylic acid isomers.

Seed crystal of higher optical purity is preferred, for example, a crystal of not less than 97%ee is more preferred, further preferred is not less than 99%ee for the purpose of obtaining azetidine-2-carboxylic acid with high optical purity.

The amount of the seed crystal of the optically active azetidine-2-carboxylic acid is not particularly limited. It is usually used not less than 0.0001% by weight to 0.1% by weight, preferably 0.001% by weight to 0.08% by weight per azetidine-2-carboxylic acid to be resolved.

The seed crystal can be added once or several times, if necessary, to the solution of azetidine-2-carboxylic acid at any time, preferably when the solution is at saturated or super-saturated region, but prior to the beginning of crystallization of the dissolved azetidine-2-carboxylic acid in the solution. Preferably it is added while cooling.

Typically, the seed crystal is added in the following manner. The seed crystal is added to a solution of azetidine-2-carboxylic acid cooled to a temperature of 1 to 30° below the temperature at which the azetidine-2-carboxylic acid was dissolved, and then the solution is further cooled or maintained at the same temperature to crystallize the desired product, preferably the solution is further cooled in terms of yield. Once the crystals begin to appear in the solution, the solution is kept standing for a while, for example, usually less than 20 hours, preferably half an hour to 10 hours, more preferably 1 to 5 hours. The crystals can be collected, for example, by filtration, whereby desired product is separated from the mixture of the optical isomers of azetidine-2-carboxylic acid.

The following Examples further illustrate the present invention in detail but are not to be construed as limiting the present invention thereto.

EXAMPLE 1

N-Benzylazetidine-2-carboxylic acid methyl ester (1.4 g) was dissolved in 40 ml of t-butyl methyl ether at 20 to 25° C. and stirred for one minute and 70 mg of Enzyme (Chirazyme L-2) suspended in 2 ml of water was poured thereto and the resulting solution was heated to 40° C. and stirred for 14 hours. Settled solution was separated into an aqueous phase and an organic phase. The aqueous phase was washed twice with t-butyl methyl ether (5 ml) to yield an aqueous solution of optically active N-benzylazetidine-2-carboxylic acid and a combined organic phase of N-Benzylazetidine-2-carboxylic acid methyl ester.

Extracted aqueous phase was subjected to high performance liquid chromatography analysis[ column: SIMICHIRAL OA-3100, 4.6 mm Φ×25 cm (Product of SUMIKA Analysis Center). Optical purity and yield of N-Benzylazetidine-2-carboxylic acid is determined and listed in Table 1 below.

EXAMPLE 2

To the aqueous solution of N-benzylazetidine-2-carboxylic acid obtained above was added 170 mg of 10% Pd(OH)$_2$ (water content: 43%) at room temperature and stirred for 18 hours under hydrogen atmosphere at room temperature, then the solution was heated to 40° C. and further stirred for 34 hours. Then, the solution was filtered to give a filtrate of azetidine-2-carboxylic acid, which was subjected to High performance liquid chromatography analysis[ column: SIMICHIRAL OA-6000, 4.6 mm Φ×15 cm (Product of SUMIKA Analysis Center), whereby the content of azetidine-2-carboxylic acid, and isomer ratio were analyzed. The ratio of (S)-isomer of optically active azetidine-2-carboxylic acid was 99.2%.

EXAMPLES 3 TO 8

4 Mg of the enzyme (commercially available) described in Table 1, 0.5 ml of 0.1M phosphate buffer solution (pH 7.0) and 0.5 ml of t-butyl methyl ether are mixed at 20° to 25° C. and the resulting mixture was stirred and then 40 mg of aqueous solution of N-benzylazetidine-2-carboxylic acid methyl ester was added thereto and heated to 40° C. and stirred for 2 hours.

Then the solution was washed with 2 ml of toluene and separated to give an aqueous phase of optically active N-benzylazetidine-2-carboxylic acid and an organic phase of N-benzylazetidine-2-carboxylic acid methyl ester. Results of the same analysis as in the Example 1 is shown in Table 1.

TABLE 1

| Ex. | Enzyme (Origin) | Yield (%) | Ratio of Isomer (S) | Ratio of Isomer (R) | Optical Purity (% ee) |
|---|---|---|---|---|---|
| 1 | Chirazyme L-2 (*Candida antarctica*) | 46.2 | 99.2 | 0.8 | 98.4 |
| 3 | Novozyme 435 (*Candida antarctica*) | 47.1 | 98.7 | 1.3 | 97.4 |
| 4 | Lipase AY (*Candida rugosa*) | 49.3 | 8.5 | 91.5 | 83.0 |
| 5 | Chirazyme L-3 (*Candida rugosa*) | 46.3 | 7.4 | 92.6 | 85.2 |
| 6 | Lipase MY (*Candida cylindracea*) | 38.6 | 7.0 | 93.0 | 86.0 |
| 7 | Lipase OF (*Candida cylindracea*) | 51.3 | 19.3 | 80.7 | 61.4 |
| 8 | Cholesterol esterase (*Candida rugosa*) | 72.8 | 32.5 | 67.5 | 35.0 |

EXAMPLE 9

4 Mg of the enzyme (ChirazymeL-2), 0.5 ml of 0.1M phosphate buffer solution (pH 7.0) and 0.5 ml of t-butyl methyl ether are mixed at 20 to 25° C. and the resulting mixture was stirred and then 40 mg of N-benzylazetidine-2-carboxylic acid methyl ester was added thereto and heated to 40° C. and stirred for 2 hours.

Then the solution was washed with 2 ml of toluene and separated to give an aqueous phase of optically active N-benzylazetidine-2-carboxylic acid and an organic phase of N-benzylazetidine-2-carboxylic acid methyl ester. Results of the same analysis as in the Example 1 is shown in Table 2.

EXAMPLES 10 TO 12

The same procedure as described in Example 9 were carried out except that a solvent described in Table 2 was used instead of t-butyl methyl ether, and an aqueous phase of optically active N-benzylazetidine-2-carboxylic acid and an organic phase of N-benzylazetidine-2-carboxylic acid methyl ester were obtained. Results of the analysis as used in the Example 1 is shown in Table 2.

TABLE 2

| Ex. | Organic Solvent | Yield (%) | Ratio of Isomer (S) | Ratio of Isomer (R) | Optical Purity (% ee) |
|---|---|---|---|---|---|
| 9 | t-butyl methyl ether | 47.1 | 98.7 | 1.3 | 97.4 |
| 10 | t-butanol | 47.4 | 97.8 | 2.2 | 95.6 |
| 11 | n-hexane | 52.4 | 95.5 | 4.5 | 91.0 |
| 12 | toluene | 33.6 | 98.9 | 1.1 | 97.8 |

EXAMPLE 13

N-Benzylazetidine-2-carboxylic acid methyl ester (1 g), 90 mg of t-butanol, 90 mg of water were mixed at 20 to 25° C. and 180 mg of Chirazyme L-2 were mixed and the resulting solution was heated to 40° C. and stirred for 2 hours. Thereafter 1 ml of water was added thereto and washed with 4 ml of t-butyl methyl ether thrice to obtain an aqueous solution of optically active N-benzylazetidine-2-carboxylic acid. Combined organic phase gave a solution of N-Benzylazetidine-2-carboxylic acid methyl ester.

Analysis was conducted as the same manner in Example 1 and the results are shown in Table 3 below.

TABLE 3

| Example | Organic Solvent | Yield (%) | Ratio of Isomer (S) | Ratio of Isomer (R) | Optical Purity (% ee) |
|---|---|---|---|---|---|
| 13 | t-butanol | 42.0 | 98.9 | 1.1 | 97.8 |

EXAMPLES 14 AND 15

4 Mg of the enzyme (commercially available) described in Table 4, 0.5 ml of 0.1M phosphate buffer solution (pH 7.0) and 0.5 ml of t-butyl methyl ether are mixed at 20 to 25° C. and the resulting mixture was stirred and then 40 mg of aqueous solution of N-[(S)-phenylethyl]azetidine-2-carboxylic acid methyl ester was added thereto and heated to 40° C. and stirred for 2 hours.

Then the solution was washed with 2 ml of toluene and separated to give an aqueous phase of optically active N-(S)-phenylethylazetidine-2-carboxylic acid and an organic phase of N-(S)-phenylethylazetidine-2-carboxylic acid methyl ester. Results of the same analysis as in the Example 1 is shown in Table 4.

TABLE 4

| Ex. | Enzyme (Origin) | Yield (%) | Ratio of Isomer (S) | Ratio of Isomer (R) | Optical Purity (% de) |
|---|---|---|---|---|---|
| 14 | Novozyme 435 (*Candida antarctica*) | 14.3 | 97.8 | 2.2 | 95.6 |
| 15 | Chirazyme L-9 (*Mucor miehei*) | 19.6 | 98.6 | 1.4 | 97.2 |

EXAMPLE 16

4 Mg of the enzyme (commercially available) described in Table 5, 2 ml of 0.1M phosphate buffer solution (pH 7.0) and 0.2 ml of n-hexane are mixed at 20 to 25° C. and the resulting mixture was stirred and then 40 mg of N-[(R)-phenylethyl]azetidine-2-carboxylic acid methyl ester was added thereto and heated to 40° C. and stirred for 9 hours.

Then the solution was washed with 2 ml of toluene and separated to give an aqueous phase of optically active N-[(R)-phenylethyl]azetidine-2-carboxylic acid and an organic phase of N-[(R)-phenylethyl]azetidine-2-carboxylic acid methyl ester. Results of the same analysis as in the Example 1 is shown in Table 5.

TABLE 5

| Ex. | Enzyme (Origin) | Yield (%) | Ratio of Isomer (S) | Ratio of Isomer (R) | Optical Purity (% de) |
|---|---|---|---|---|---|
| 16 | Novozyme 435 (*Candida antarctica*) | 50.1 | 96.4 | 3.6 | 92.8 |

EXAMPLE 17

4 Mg of the enzyme (commercially available) described in Table 6, and 2 ml of 0.1M phosphate buffer solution (pH 7.0) are mixed at 20 to 25° C. and the resulting mixture was stirred and then 40 mg of N-[(R)-phenylethyl]azetidine-2-carboxylic acid methyl ester was added thereto and heated to 40° C. and stirred for 2 hours.

Then the solution was washed with 2 ml of toluene and separated to give an aqueous phase of optically active N-[(R)-phenylethyl]azetidine-2-carboxylic acid and an organic phase of N-[(R)-phenylethyl]azetidine-2-carboxylic acid methyl ester. Results of the same analysis as in the Example 1 is shown in Table 6.

TABLE 6

| Ex. | Enzyme (Origin) | Yield (%) | Ratio of Isomer (S) | Ratio of Isomer (R) | Optical Purity (% de) |
|---|---|---|---|---|---|
| 17 | Lipase OF (*Candida cylindracea*) | 59.4 | 22.5 | 77.5 | 55.0 |

EXAMPLE 18

Azetidine-2-carboxylic acid (8.59 g; L-isomer, 86.8%ee) was added to a mixed solvent of 18.0 g of water and 54.0 g of methanol and completely dissolved at 70° C. The solution was cooled to 60° C. at 8° C./hr and a seed crystal of L-azetidine-2-carboxylic acid (0.5 mg, optical purity: 99.9%ee) was added thereto and further cooled at the same rate to −10° C., and further maintained at the same temperature for 2 hours to yield crystals of L-azetidine-2-carboxylic acid.

The crystalline product was collected by filtration to give L-azetidine-2-carboxylic acid (5.64 g; L-isomer >99.9%ee). (Yield based on the charged azetidine-2-carboxylic acid; 66%, Yield based on the L-azetidine-2-carboxylic acid:70%)

EXAMPLE 19

Azetidine-2-carboxylic acid (4.81 g; L-isomer, 88.3%ee) was added to a mixed solvent of 12.1 g of water and 62.2 g of methanol and completely dissolved at 70° C. The solution was cooled to 65° C. at 8° C./hr and a seed crystal of L-azetidine-2-carboxylic acid (0.5 mg, optical purity: 99.9%ee) was added thereto and further cooled at the same rate to −2° C., and further maintained at the same temperature for 2 hours to yield crystals of L-azetidine-2-carboxylic acid.

The crystalline product was collected by filtration to give L-azetidine-2-carboxylic acid (3.33 g; L-isomer >99.9%ee). (Yield based on the charged azetidine-2-carboxylic acid: 69%, Yield based on the L-azetidine-2-carboxylic acid: 74%)

EXAMPLE 20

Azetidine-2-carboxylic acid (3.76 g; L-isomer, 94.0%ee) was added to a mixed solvent of 7.3 g of water and 20.5 g of methanol and completely dissolved at 70° C. The solution was cooled to 65° C. at 8° C./hr and a seed crystal of L-azetidine-2-carboxylic acid (0.5 mg, optical purity: 99.9%ee) was added thereto and further cooled at the same rate to −2° C., and further maintained at the same temperature for 4 hours to yield crystals of L-azetidine-2-carboxylic acid.

The crystalline product was collected by filtration to give L-azetidine-2-carboxylic acid (2.68 g; L-isomer >99.9%ee). (Yield based on the charged azetidine-2-carboxylic acid; 71%, Yield based on the L-azetidine-2-carboxylic acid: 73%)

EXAMPLE 21

Azetidine-2-carboxylic acid (9.12 g; L-isomer, 89.9%ee) was added to a mixed solvent of 16.6 g of water and 74.6 g of ethanol and completely dissolved at 80° C. The solution was cooled to 70° C. at 7° C./hr and a seed crystal of L-azetidine-2-carboxylic acid (1 mg, optical purity: 99.9%ee) was added thereto and further cooled at the same rate to 0° C., and further maintained at the same temperature for 2 hours to yield crystals of L-azetidine-2-carboxylic acid.

The crystalline product was collected by filtration to give L-azetidine-2-carboxylic acid (5.95 g; L-isomer >99.9%ee). (Yield based on the charged azetidine-2-carboxylic acid: 65%, Yield based on the L-azetidine-2-carboxylic acid: 69%)

EXAMPLE 22

Azetidine-2-carboxylic acid (31.6 g; D-isomer, 74.9%ee) was added to a mixed solvent of 41.6 g of water and 230.9 g of methanol and completely dissolved at 67° C. The solution was cooled to 65° C. at 10° C./hr and a seed crystal of D-azetidine-2-carboxylic acid (1 mg, optical purity: 99.9%ee) was added thereto and further cooled at the same rate to 0° C., and further maintained at the same temperature for 2 hours to yield crystals of D-azetidine-2-carboxylic acid.

The crystalline product was collected by filtration to give D-azetidine-2-carboxylic acid (14.2 g; D-isomer >99.9%ee). (Yield based on the charged azetidine-2-carboxylic acid: 45%, Yield based on the D-azetidine-2-carboxylic acid: 51%)

EXAMPLE 23

21.02 g of N-Benzylazetidine-2-carboxylic acid methyl ester, 592 g of t-butyl methyl ether and 40 g of water are mixed at 20 to 25° C. and then 1.41 g of enzyme (Chirazyme L-2) was added thereto and the resulting solution was heated to 40° C. and stirred for 14 hours. Settled solution was separated into an aqueous phase and an organic phase. The aqueous phase was washed twice with t-butyl methyl ether to yield an aqueous solution of optically active N-benzylazetidine-2-carboxylic acid and a combined organic phase of N-benzylazetidine-2-carboxylic acid methyl ester. Results of the same analysis as in the Example 1 is shown in Table 7.

TABLE 7

| Ex. | Organic Solvent | Yield (%) | Ratio of Isomer (S) | Ratio of Isomer (R) | Optical Purity (% ee) |
|---|---|---|---|---|---|
| 23 | t-butyl methyl ether | 43.8 | 99.6 | 0.4 | 99.2 |

EXAMPLE 24

10.0 g of N-Benzylazetidine-2-carboxylic acid ethyl ester, 29.6 g of t-butyl methyl ether and 26.7 g of water are mixed at 20 to 25° C. and then 0.333 g of Enzyme (Chirazyme L-2) was added thereto and the resulting solution was heated to 40° C. and stirred for 7 hours. Settled solution was separated into an aqueous phase and an organic phase. The aqueous phase was washed twice with t-butyl methyl ether to yield an aqueous solution of optically active N-benzylazetidine-2-carboxylic acid and a combined organic phase of N-benzylazetidine-2-carboxylic acid ethyl ester. Results of the same analysis as in the Example 1 is shown in Table 8.

TABLE 8

| Ex. | Enzyme (Origin) | Yield (%) | Ratio of Isomer (S) | Ratio of Isomer (R) | Optical Purity (% ee) |
|---|---|---|---|---|---|
| 24 | Chirazyme L-2 (*Candida antarctica*) | 44.4 | 99.2 | 0.8 | 98.4 |

What is claimed is:

1. A process for producing N-substituted azetidine-2-carboxylic acid of the formula I:

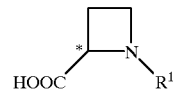

wherein $R^1$ denotes an aralkyl group of an arylated lower alkoxycarbonyl group and * designates an asymmetric carbon atom, which comprises:

reacting an N-substituted azetidine-2-carboxylic acid ester of the formula II:

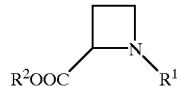

wherein $R^1$ has the same meaning as defined above and $R^2$ denotes an alkyl group, an aralkyl group or an allyl group, with an enzyme derived from a microorganism belonging to Candida, Mucor, Humicola, Rhizopus, Aspergillus, Penicillium, Bacillus, Arthrobacter, Pseudomonas, Chromobacterium, Alkaligenes or Achromobacter, and capable of selectively hydrolyzing a stereoisomer based on the carbon atom of the 2-position of the azetidine ring in the presence of an organic solvent.

2. The process according to claim 1, wherein the amount of the organic solvent used is not more than 100 times by weight based on the weight of used N-substituted azetidine-2-carboxylic acid ester.

3. The process according to claim 1, wherein the organic solvent to be used is at least one solvent selected from a hydrophobic organic solvent and a hydrophilic organic solvent.

4. A process according to any one of claims 1, 2 or 3, which further comprises reacting the optically active N-substituted azetidine-2-carboxylic acid of the formula I with a reducing agent in the presence of a catalyst to produce an optically active azetidine-2-carboxylic acid of the formula III:

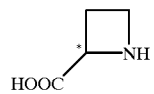

wherein * designates an asymmetric carbon atom.

5. A process according to claim 4, which comprises further steps for improving optical purity of azetidine-2-carboxylic acid of the formula III as defined in claim 4, which steps comprise:

preparing a solution of said azetidine-2-carboxylic acid; and cooling said solution in the presence of a seed crystal of one optional optical isomer of the azetidine-2-carboxylic acid to selectively recrystallize the optical isomer of the azetidine-2-carboxylic acid having the same configuration with respect to the carbon atom of the 2-position of the azetidine ring as the seed crystal.

6. The process according to claim 5, wherein the solvent is water, a water miscible organic solvent or a mixture thereof.

7. The process according to claim 6, wherein the water miscible solvent is an alcohol.

8. The process according to claim 7, wherein the alcohol is methanol or ethanol.

9. The process according to claim 4, wherein the reducing agent is hydrogen, hydrazine or a salt thereof, formic acid or a salt thereof.

* * * * *

UNITED STATES PATENT AND TRADEMARK OFFICE
CERTIFICATE OF CORRECTION

PATENT NO.   : 6,162,621
DATED        : December 19, 2000
INVENTOR(S)  : Kudo et al.

It is certified that error appears in the above-identified patent and that said Letters Patent is hereby corrected as shown below:

Column 12,
Line 21, change "of" to -- or --

Signed and Sealed this

Twenty-fifth Day of September, 2001

*Attest:*

*Nicholas P. Godici*

NICHOLAS P. GODICI
*Attesting Officer*   *Acting Director of the United States Patent and Trademark Office*